United States Patent
Levandowski et al.

(10) Patent No.: US 6,630,233 B1
(45) Date of Patent: Oct. 7, 2003

(54) DEVICE FOR FRESHENING EXHAUST FROM VACUUM CLEANERS

(76) Inventors: John Levandowski, 3074 Arns, Oakland, MI (US) 48363; Elizabeth Levandowski, 3074 Arns, Oakland, MI (US) 48363

( * ) Notice: Subject to any disclaimer, the term of this patent is extended or adjusted under 35 U.S.C. 154(b) by 0 days.

(21) Appl. No.: 09/221,103

(22) Filed: Dec. 28, 1998

Related U.S. Application Data

(63) Continuation-in-part of application No. 07/908,953, filed on Jul. 6, 1992, now abandoned.

(51) Int. Cl.[7] .............................. B32B 3/26; A62B 7/08
(52) U.S. Cl. ..................... 428/321.5; 422/122
(58) Field of Search .................. 422/122; 428/321.5

(56) References Cited

U.S. PATENT DOCUMENTS

| | | | |
|---|---|---|---|
| 3,632,396 A | * | 1/1972 | Perez-Zamora ............. 427/242 |
| 4,917,920 A | * | 4/1990 | Ono et al. ................. 427/389.9 |
| 5,419,958 A | * | 5/1995 | Charbonneau ............ 428/315.5 |
| 5,607,754 A | * | 3/1997 | Giles et al. ................. 428/211 |
| 5,798,315 A | * | 8/1998 | Etoh et al. ................. 503/215 |

* cited by examiner

Primary Examiner—Cynthia H. Kelly
Assistant Examiner—J. M. Gray
(74) Attorney, Agent, or Firm—Lynn E. Cargill

(57) ABSTRACT

Devices and methods using freshening agents, such as perfumes, synthetic fragrances, deodorizers, fragrance fixing agents or mixtures thereof, for freshening the air exhausting from a vacuum cleaner during operation. One embodiment includes a thin, flexible sheet capable of being vacuumed into a vacuum cleaner, wherein the sheet has the freshening agent bound thereto. Methods for utilizing such a device are also disclosed. A second embodiment includes a disposable vacuum cleaner bag wherein at least a portion of the vacuum cleaner bag has the freshening agent bound thereto. A third embodiment includes a tubular collar to be affixed to the inlet tube of a vacuum cleaner, wherein the collar has the freshening agent bound thereto. The applied fragrance shall have a higher or greater impact on the olfactory senses of the vacuum cleaner operator than does the malodorous exhaust.

1 Claim, 1 Drawing Sheet

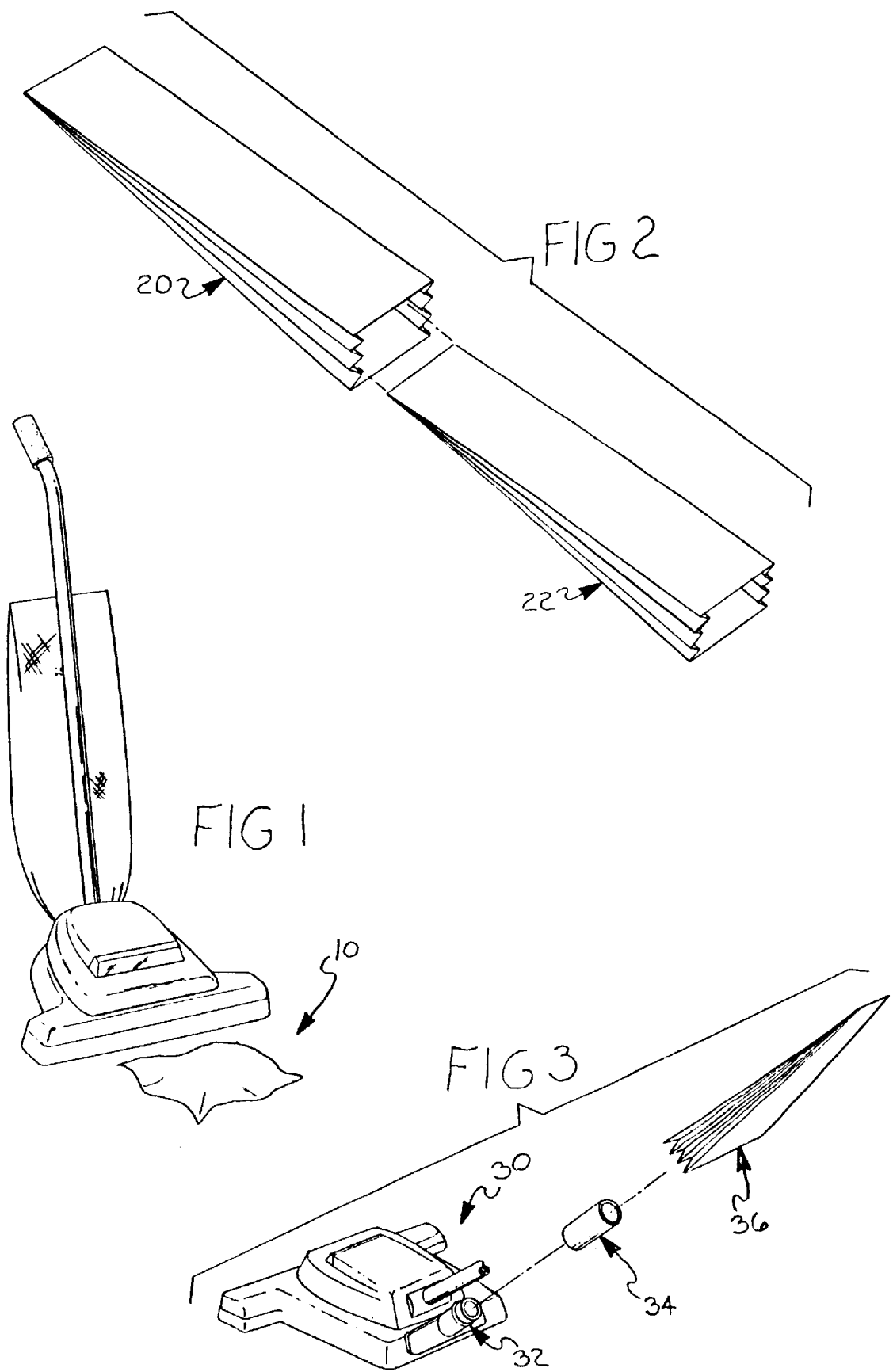

DEVICE FOR FRESHENING EXHAUST FROM VACUUM CLEANERS

This application is a continuation in part of application Ser. No. 07/908,953 filed Jul. 6, 1992 now abandoned.

TECHNICAL FIELD

This invention relates generally to devices and methods for freshening the air exhausting from vacuum cleaners during operation.

BACKGROUND OF THE INVENTION

As is well known, vacuuming with a vacuum cleaner is used to rid the house or workplace of unsightly dirt and odor-causing elements, such as dust, animal fur, and tobacco ashes, and collect them in a vacuum cleaner bag. However, as the odor-causing elements are permitted to remain in the vacuum cleaner bag, objectionable odors frequently develop. With the disposable vacuum cleaner bags which are in wide use today, it is not intended that they be emptied periodically to rid them of the objectionable odors, because the main advantage of the disposable vacuum bags is the fact that they may be thrown away with the dirt contained therein. Hence, should objectionable odors emanate from such a disposable bag before it is filled, it may be necessary to dispose of it before its full use has been realized. This results in a reduction of the useful life of the disposable bag with a corresponding increase in the cost of maintaining the vacuum cleaner supplied with disposable bags.

An example of a previous attempt at eliminating the odors from disposable vacuum cleaner bags was disclosed in U.S. Pat. No. 3,274,758 to Parman. The disposable vacuum cleaner dust containers disclosed include an envelope made of a thin film and filled with a deodorizing material in solid form. When the disposable dust container is placed into position on the vacuum cleaner, the envelope ruptures, releasing the deodorizing material into the disposable dust container. The disposable dust container disclosed, however, is complex and difficult to manufacture.

In addition, Parman discusses that it has also been suggested that the material of the bag be impregnated with a deodorant at the time of manufacture. However, Parman continues to explain that deodorants are volatile and would be substantially or entirely dissipated before the bag reached the user.

Other solutions to the problem include scented granules or beads which are to be placed inside the disposable vacuum cleaner bag to scent the air emanating from the vacuum cleaner. However, these products are often difficult and messy to use.

Examples of other previous attempts to solve the problem are described in the following patents:

U.S. Pat. Nos. 2,574,578 issued Nov. 13, 1951 and 2,179,665 issued Nov. 14, 1939 to Martinet disclose a crystal grinder attachment for suction cleaners. Although the principal object of the patented inventions is to grind moth crystals to be sprayed out of a blower tool which is attached to the cleaner, the patents also include disclosure of the inclusion of a chemical reagent for purifying or fumigating floor coverings, clothes and the like.

U.S. Pat. No. 2,304,868 issued Dec. 15, 1942 to Winthrop discloses a vacuum cleaner which sprays atomized liquid into the air and dust which is drawn up into the vacuum cleaner. The liquid is to be of a character which will act as a deodorizer, a disinfectant or the like.

U.S. Pat. No. 2,152,277 issued Mar. 28, 1939 to Pierce discloses a suction cleaner which includes an odorizing unit which is an automatic ejector-type odorizer unit.

It is, therefore, a primary object of the present invention to provide devices and methods which eliminate, reduce, or mask the offensive smell of house dust, stale tobacco, and pet odors from a vacuum cleaner's exhaust. It is another object of the present invention to provide such devices which are easy to manufacture, easy and tidy to use, and do not require specially-designed vacuum cleaners or vacuum cleaner bags.

SUMMARY OF THE INVENTION

In accordance with the preferred embodiment of the invention, these and other objects and advantages are addressed as follows. A device for freshening the air exhausting from a vacuum cleaner during operation is disclosed which includes (a) a thin, flexible sheet formed of a material and having dimensions so that the sheet is capable of being vacuumed into the vacuum cleaner without damaging the vacuum cleaner and (b) an agent bound to the sheet selected from the group consisting of a perfume, a synthetic fragrance, a deodorizer, and mixtures thereof, the agent being in a form such that the agent increasingly activates with increasing air flow around the sheet, thereby freshening the air being exhausted from the vacuum cleaner.

The invention also provides a method for freshening the air exhausting from a vacuum cleaner during operation, which entails (a) vacuuming into the vacuum cleaner the thin, flexible sheet described above and (b) operating the vacuum cleaner so that increased of air flow passes by the sheet inside the vacuum cleaner and activates the agent on the sheet, thereby freshening the air being exhausted from the vacuum cleaner.

The flexible sheet may be disintegratable so as not to harm the vacuum cleaner, or so that the fragrance and/or deodorizer contacting the sheet may be subjected to a continuous fresh surface.

Fragrances which may contact the flexible sheet can be affixed to the sheet by spraying, soaking, or any other method known in the art. For certain fragrances or certain sheet materials, a fixing agent may also be required in order to keep the fragrance on the sheet. Thus, a fragrance is contacted to the sheet and also "fixed" to the sheet with a fixing agent.

Perfumes or other synthetic fragrances have a subjective quality known in the art as "impact", meaning the effect the fragrance has on the olfactory sense of the vacuum cleaner operator. For example, the fragrances of cherry and cinnamon have a high "impact" in that a small amount of the fragrance is necessary in an item in order for the scent to be very noticeable. On the other hand, the scent of vanilla has a low impact so a large concentration of the fragrance is necessary in order to be noticed. Other considerations include the various "notes" that a fragrance imparts. The "high note" is the initial fragrance that hits your nose, while the "mid-note" is the fragrance which levels off, and the "base note" is the fragrance that holds the scent together.

The present invention seeks to provide a sufficient amount of fragrance, between 2 and 20 percent, based upon either the weight of the fragrance itself or the fragrance and the fixing agent, of the overall weight of the flexible sheet, the fragrance and the fixing agent (if used). The amount of fragrance will vary depending upon the scent being utilized, such as the cherry or cinnamon scent versus the vanilla scent mentioned above. The applied fragrance must have a higher or greater impact than the malodorous exhaust in order to be effective to the vacuum cleaner operator. In other words, the applied scent must be stronger than the exhaust smell in order to work effectively.

A second type of device disclosed is a disposable vacuum cleaner bag for freshening the air exhausting from a vacuum cleaner during operation which includes at least a portion of the vacuum cleaner bag having an agent bound thereto selected from the group consisting of a perfume, a deodorizer, and mixtures thereof, the agent being in a form such that the agent increasingly activates with increasing air flow through the vacuum cleaner bag, thereby freshening the air exhausting from the vacuum cleaner.

A third type of a device disclosed for freshening the air exhausting from a vacuum cleaner is affixed to the inlet tube for air entering a vacuum cleaner bag during operation. The device includes a tubular collar having two open ends, the collar to be affixed to the inlet tube of the vacuum cleaner and extend outwardly therefrom, the collar having an agent bound thereto selected from the group consisting of a perfume, a deodorizer, and mixtures thereof, the agent being in a form such that the agent increasingly activates with increasing air flow around the collar, thereby freshening the air being exhausted from the vacuum cleaner.

BRIEF DESCRIPTION OF THE DRAWINGS

The nature and extent of the present invention will be clear from the following detailed description of the particular embodiments thereof, taken in conjunction with the appendant drawings, in which:

FIG. 1 shows a perspective view of a vacuum cleaner and one embodiment of the invention which consists primarily of a flexible sheet having a freshening agent bound thereto;

FIG. 2 illustrates another embodiment of the invention in which a disposable vacuum bag has a liner with a freshening agent bound thereto; and FIG. 3 illustrates a portion of a vacuum and yet another embodiment of the invention which includes a collar to be affixed to the tube of a vacuum cleaner which directs air into the vacuum cleaner bag.

DETAILED DESCRIPTION OF THE INVENTION

The invention includes three different device embodiments and their variations for freshening the air exhausting from a vacuum cleaner during operation. All of the devices use a freshening agent, such as a perfume, synthetic fragrances, micro-encapsulated perfumes or synthetic fragrances, fixing agents selected from the group consisting of waxes, organic materials and polymers, a deodorizer, or mixtures thereof which is released into the exhaust air of the vacuum cleaner especially in the presence of increased air flow. Preferably, the freshening agent is in a form which provides controlled release of the freshening agent into the air.

As mentioned, the freshening agent may be a perfume or a mixture of perfumes, such as those having an herbal, pine, spice, or citrus odor. The freshening agent may also be a synthetic fragrance or a collection of synthetic fragrances. Depending upon the fragrance or perfume used, a fixing agent may be necessary. The fixing agents are well known in the art, and can be matched to specific materials and fragrances without undue experimentation. The fixing agent may be selected from the group consisting of waxes, organic materials and polymers and are readily available on the marketplace. Fixing agents may also be specific to the sheet material upon which the freshening agent is being contacted. For example, scents may easily be incorporated into a plastic sheet, without the need for much of a fixing agent. However, if a paper and/or cotton sheet is utilized, a fixing agent will likely be needed.

The freshening agent may contact the sheet at a concentration of between about 2 and about 20 weight percent based upon the overall weight of the combined sheet and the freshening agent. This may mean that the freshening agent has a combined weight of a synthetic fragrance and a fixing agent, and that this combined weight could be as much as 20 weight percent based on the overall weight of the combined sheet and freshening agent.

The impact of the freshening agent must be greater than the impact of the malodorous exhaust in order for invention to work properly. In the event that a deodorizer is used, such as an enzymatic odor eliminator, then the impact of the malodorous exhaust shall have been reduced to such a level as to not be offensive. Enzymatic odor eliminators work by breaking up the aromatic portions of ring hydrocarbons, in the case of organic smells. As such, the enzymatic odor eliminators work to open up the aromatic rings so as to render them into aliphatic hydrocarbon chains, which do not have the same impact as the aromatic compounds. The freshening agent may also be a deodorizer, including non-volatile deodorizers, such as baking powder or other odor absorbent material. The devices of this invention may also include a combination of one or more perfumes with one or more deodorizers.

FIG. 1 illustrates a common type of vacuum cleaner alongside a freshening device, denoted by the numeral 10, which generally consists of a thin, flexible sheet formed of a material and having dimensions so that the sheet may be vacuumed into the vacuum cleaner without damaging the vacuum cleaner. The sheet has a freshening agent as discussed above bound thereto. The freshening agent is in a form such that the agent increasingly activates with increasing air flow around the sheet. Therefore, when the sheet is vacuumed inside the vacuum cleaner, the agent freshens the air exhausting from the vacuum cleaner during operation.

The sheet may be formed of a paper product, cotton, or polyester or other polymeric product. The sheet may advantageously be made of a disintegratable material in order to constantly expose fresh surfaces of the material component. These fresh surfaces will expose fresh fragrance or deodorizing agent, and air circulating thereby will activate the freshening agent fragrance or deodorizer, acting in accordance with the present invention. The weight and consistency of the sheet shall be adaptable for the purpose of being vacuumed up into a vacuum cleaner without harming it. For example, the sheet could weigh between about 5 and about 50 grams overall weight with the freshening agent contacted thereto. The preferred weight and consistency is that of a normal facial tissue, although a range of weights and materials are to be anticipated by the present invention. Depending on the construction of the sheet, air may flow through the sheet or merely around it. The sheet may vary widely in dimensions, however, sheets having the thickness of household paper products, such as tissue paper, paper towels, toilet paper, or napkins, would be suitable.

The freshening agent may be embedded into and/or coated on the sheet. Preferably, the freshening agent is encapsulated by or in admixture with a commercially available controlled release material. In this form the freshening agent will last longer, being activated primarily in the presence of increased air flow.

The freshening sheet is tidy and easy to use, requiring no measuring. It may be packaged in a pop-up dispenser packaging for easy dispensing.

To use the freshening sheets of this invention, the freshening sheet is merely vacuumed into the vacuum cleaner, and, during operation, the freshening sheet will be activated to scent and/or deodorize the air exhausting from the vacuum cleaner. The number of freshening sheets one uses between emptying or changing the vacuum cleaner bag depends on how often one vacuums and the desired fragrance and/or deodorizing level.

Referring next to FIG. 2, disposable vacuum cleaner bag 20 is shown having liner 22 which has a freshening agent as described above bound thereto. A variation of the concept includes that all or a portion of a disposable vacuum cleaner bag without a liner has the freshening agent bound thereto.

The disposable vacuum cleaner bag may be formed of paper, cotton, or polyester or other polymeric material. The freshening agent may be embedded into the vacuum cleaner bag or liner and/or coated thereon. Preferably, the freshening agent is encapsulated by or in admixture with a controlled release material.

To use the embodiment of FIG. 2, disposable vacuum cleaner bag 20 with liner 22 is merely placed in position on the vacuum cleaner. During operation of the vacuum cleaner, air flows through the disposable vacuum cleaner bag and becomes freshened.

Turning now to FIG. 3, there is shown a portion of an upright vacuum cleaner generally denoted by the numeral 30 having inlet tube 32. Inlet tube 32 directs air from the intake of the vacuum cleaner to the vacuum cleaner bag. An embodiment of the invention is shown which consists of collar 34 to be affixed to inlet tube 32. Collar 34 has a freshening agent as described above bound thereto. Collar 34 may be sized to press fit over or inside inlet tube 32 and to extend partially therefrom. Collar 34 may be formed to be stiff or flexible material and may be formed of, e.g., a paper product, such as cardboard; cotton; or polyester or other polymeric product. Collar 34 may be formed of layers of material having the freshening agent bound thereto or may contain several layers of material with the freshening agent sandwiched between the layers. On the other hand, collar 34 may be a solid, non-layered construction with the freshening agent embedded therein and/or coated thereon. Preferably, the freshening agent is encapsulated by or in admixture with a controlled release material.

To use collar 34, collar 34 is press-fit to inlet tube 32 of vacuum cleaner 30. Thereafter, reusable or disposable vacuum cleaner bag 36 is placed over collar 34 and onto inlet tube 32. Vacuum cleaner bag 36 is secured as usual and the vacuum cleaner is ready for operation. This embodiment of the invention is especially effective because the highest air flow rate occurs at the inlet tube. Depending on the construction of collar 34, air may flow through or merely around the collar.

A variation of the embodiment of FIG. 3 is a freshening device which includes a collar attached to a disposable vacuum cleaner bag at the bag's opening or inlet end. The attached collar would have a freshening agent as described above bound thereto and be sized so that once it is attached to the air inlet tube of a vacuum cleaner, the collar would extend therefrom. The collar may be sized to be press fit over or inside the air inlet tube of a vacuum cleaner and may be of the same construction as that described for collar 34 of FIG. 3.

To use this variation, the collar/disposable vacuum cleaner bag combination is attached to the air inlet tube of a vacuum cleaner. During operation of the vacuum cleaner, air flowing by and/or through the collar becomes freshened.

In all three general embodiment types, it is most desirable to package them in vapor-impervious containers to minimize the loss or deactivation of the freshening agent. In addition, if several freshening devices are included in one package, it would be best to use resealable packaging, so the user may reseal the package, thereby minimizing the loss or deactivation of the freshening agent.

Thus, there is provided in accordance with the present invention, devices and methods which eliminate, reduce, or mask offensive odors generated in vacuum bags. The devices provided are easy to make, easy and tidy to use, and do not require specially-designed vacuum cleaners or vacuum cleaner bags.

While our invention has been described in terms of a specific embodiment, it must be appreciated that other embodiments could readily be adapted by one skilled in the art. Accordingly, the scope of our invention is to be limited only by the following claims.

What is claimed is:

1. A vacuum cleaner freshening article to be vacuumed up by a vacuum cleaner for freshening the air exhausting from the vacuum cleaner during its operation, comprising:

(a) a flexible sheet formed of a material selected from the group consisting of cotton, polyester and other polymeric products, such that the sheet is capable of being vacuumed into the vacuum cleaner without damaging the vacuum cleaner;

(b) at least one freshening agent contacting all of the surface of the sheet, said freshening agent being selected from the group consisting of perfumes; and synthetic fragrances, the freshening agent being in a form which increasingly activates with increasing air flow around the sheet, whereby the air being exhausted from the vacuum cleaner is freshened after the sheet has been vacuumed into the vacuum cleaner; and (c) at least one fixing agent for fixing the freshening agent to the flexible sheet, said fixing agent also contacting all of the surface of the sheet and being selected from the group consisting of waxes, organic materials and polymers, deodorizers, non-volatile odor-absorbent materials, and mixtures thereof;

(d) said freshening agent and fixing agent contacting the sheet being incorporated at a concentration of between about 2 and about 20 weight percent based upon the overall weight of the combined sheet and the freshening agent and fixing agent combination, such that the impact of the malodorous exhaust from the vacuum cleaner is reduced to a level of at least less than freshening agent, and wherein said sheet weighs between about 5 and 50 grams overall weight of the combination of the flexible sheet and the freshening agent.

* * * * *